(12) United States Patent
Periasamy et al.

(10) Patent No.: US 12,000,791 B2
(45) Date of Patent: Jun. 4, 2024

(54) RNA PROFILING DEVICE AND METHOD

(71) Applicant: UNIVERSITI MALAYA, Kuala Lumpur (MY)

(72) Inventors: Vengadesh Periasamy, Kuala Lumpur (MY); Maryam Rajabpour Niknam, Kuala Lumpur (MY); Nastaran Rizan, Kuala Lumpur (MY); Sara Talebi, Kuala Lumpur (MY)

(73) Assignee: UNIVERSITI MALAYA, Kuala Lumpur (MY)

(*) Notice: Subject to any disclaimer, the term of this patent is extended or adjusted under 35 U.S.C. 154(b) by 1207 days.

(21) Appl. No.: 16/618,768

(22) PCT Filed: May 30, 2018

(86) PCT No.: PCT/MY2018/000018
§ 371 (c)(1),
(2) Date: Dec. 2, 2019

(87) PCT Pub. No.: WO2018/222026
PCT Pub. Date: Dec. 6, 2018

(65) Prior Publication Data
US 2021/0080417 A1    Mar. 18, 2021

(30) Foreign Application Priority Data
May 30, 2017    (MY) .......................... PI 2017701978

(51) Int. Cl.
*G01N 27/327* (2006.01)
*C12Q 1/6825* (2018.01)
(Continued)

(52) U.S. Cl.
CPC ......... *G01N 27/129* (2013.01); *C12Q 1/6825* (2013.01); *G01N 27/4145* (2013.01);
(Continued)

(58) Field of Classification Search
CPC ........... G01N 27/129; G01N 33/48707; G01N 27/414; G01N 27/4145; C12Q 1/6825; C12Q 2563/116; C12Q 2565/607
See application file for complete search history.

(56) References Cited

U.S. PATENT DOCUMENTS

2008/0035494 A1    2/2008  Gomez et al.
2011/0316565 A1*  12/2011  Guo .................... G01N 27/4146
                                                             257/253
2012/0073992 A1    3/2012  Kim et al.

FOREIGN PATENT DOCUMENTS

EP        2100849 A1 *  9/2009  ............... B81C 1/00
WO    2016/030713 A1     3/2016

OTHER PUBLICATIONS

Güllü et al., "electronic parameters of MIS Schottky diodes with DNA biopolymer interlayer," Materials Science-Poland, 33(3), 2015, pp. 593-600 (Year: 2015).*

(Continued)

*Primary Examiner* — Alexander S Noguerola
(74) *Attorney, Agent, or Firm* — John Hocker; Cybernetic Law PLLC

(57) ABSTRACT

The present invention provides device for profiling a biological sample with at least one RNA segment comprising: a metal wire positioned relative to the biological sample such that the sample and the metal wire form a Schottky barrier junction; a bias voltage provider adapted for rectifying the Schottky junction; and; a module for collecting the current over voltage profile of the Schottky junction.

17 Claims, 2 Drawing Sheets

Figure 1:
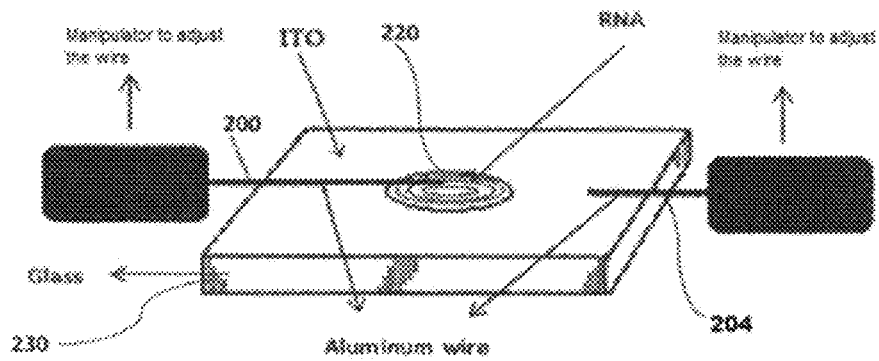

(51) Int. Cl.
    *G01N 27/12*     (2006.01)
    *G01N 27/414*     (2006.01)
    *G01N 33/487*     (2006.01)
    *H01L 29/47*     (2006.01)

(52) U.S. Cl.
    CPC . *G01N 33/48707* (2013.01); *C12Q 2563/116* (2013.01); *C12Q 2565/607* (2013.01)

(56) References Cited

OTHER PUBLICATIONS

Alamoudi et al., "DNA Profiling Methods and Tools: A Review," ICST Institute for Computer Sciences, Social Informatics and Telecommunications Engineering 2018 R. Mehmood et al. (Eds.): SCITA 2017, LNICST 224, pp. 216-231, 2018 (Year: 2018).*

Periasamy et al, Measuring the Electronic Properties of DNA-specific Schottky Diodes Towards Detecting and Identifying Basidiomycetes DNA, Sci. Rep. 6, 29879, DOI: 10.1038/srep29879, pp. 1-9, Jul. 20, 2016 including supplemental information (Year: 2016).*

Helmenstine, Anne Marie, Ph.D. "The Differences Between DNA and RNA." ThoughtCo, Apr. 5, 2023, thoughtco.com/dna-versus-rna-608191 (Year: 2023).*

Periasamy, V. et al., "Measuring the Electronic Properties of DNA-Specific Schottky Diodes Towards Detecting and Identifying Basidiomycetes DNA," Scientific Reports 6, Article No. 29879, pp. 1-9 (Jul. 2016).

Zang, D.Y. & Grote, J.G., "Photoelectrical effect and current-voltage characteristics in DNA-metal Schottky barriers," Organic Photonic Materials and Devices IX, Proc. SPIE 6470, pp. 1-10 (Feb. 2007).

* cited by examiner

RNA PROFILING DEVICE AND METHOD

FIELD OF INVENTION

The present invention generally relates to bio-electronics, and more particularly to RNA-based electronic devices.

BACKGROUND

The electronics industry is constantly transforming as new technologies develops and enter the market, thereby quickly rendering older technologies obsolete. Accordingly, new challenges emerges, however only to indicate that there is a steady need for advanced electronics; whereby their deployment can vary from solar cells, microwave diodes, to photodetectors. One of the primary challenges in accommodating the constant state of flux and huge developments in the electronics industry is the limitation in conventional materials hence the need to identify suitable alternatives for these materials.

Semiconductors are one of the many primary components that play a significant role in advanced electronic devices. The impact of semiconductors m human daily lives is immense, continuously providing renewed attention to industries ranging from telecommunication to automotive with every advancement that necessitates their role. In recent decades, organic or hybrid semiconductors have been introduced in electrical and optoelectronic applications in response to the increasing demand for sustainable electronic solutions. A pertinent example is the inclusive of deoxyribonucleic acid (DNA) in the design and production of novel hybrid semiconductor devices such as photovoltaic devices and diodes. Other materials such as conductive polymers and organic compounds have also been shown to achieve rectifying junctions like metal and inorganic semiconductors, however a great majority of these solutions are undergoing intensive research.

Similarly, extensive studies on ribonucleic acid (RNA) during the past decade have revealed new findings on the critical roles in all living cells. Recently discovered types of RNA proved to have numerous other crucial functions in controlling gene expression such as how and when information from DNA is transcribed into mRNA, and then translated into proteins. It would be advantageous to develop a technology that leverages on the properties of RNA that could extend beyond or overcome conventional semiconductors limitations.

SUMMARY OF INVENTION

In one aspect, the present invention discloses a device for profiling a biological sample with at least one RNA segment comprising: a metal wire positioned relative to the biological sample such that the sample and the metal layer form a Schottky barrier junction; a bias voltage provider adapted for rectifying the Schottky junction; and; a module for collecting the current over voltage profile of the Schottky junction.

Preferably, bias voltage provider is adapted for providing a forward or reverse bias voltage.

Preferably, the biological sample is an RNA layer.

Preferably, the biological sample is supported by a glass or any hard or flexible solid substrates.

Preferably, the positive bias voltage is provided within the range of 0 to 3V. It is anticipated, however that other detection or sensing regions may also be present within other bias range, Negative bias voltage may include up to any breakdown voltage in the negative region.

Preferably, the bias voltage provider includes a metal wire.

Advantageously, the device is able to generate varying quantitative response based on varying bias voltage; subject to the RNA fragment.

Preferably, the Schottky junction can be of p-n or n-p junction, depending on the type of RNA fragment being profiled.

Preferably, the substrate layer can be selected from the following group of materials: Indium Tin Oxide (ITO), Tin Oxide ($SnO_2$).

Advantageously, the metal wire is a conductive material; whereby it can be selected from the group of materials: aluminium (Al), Aurum (Au), Cuprum (Cu) or any other metals.

In a further aspect, there is provided a method for profiling a biological sample comprising at least one RNA fragment isolated from a subject comprising: providing a metal layer adjacent to the RNA fragment, in a manner such that they form a Schottky barrier junction; providing a bias voltage to the Schottky junction; and collecting current over voltage profile of said Schottky junction.

Preferably, bias voltage provided is sufficient to rectify the biological sample; whereby the bias voltage provided is a forward or, a reverse bias.

BRIEF DESCRIPTION OF FIGURE(S)

Figure 2:
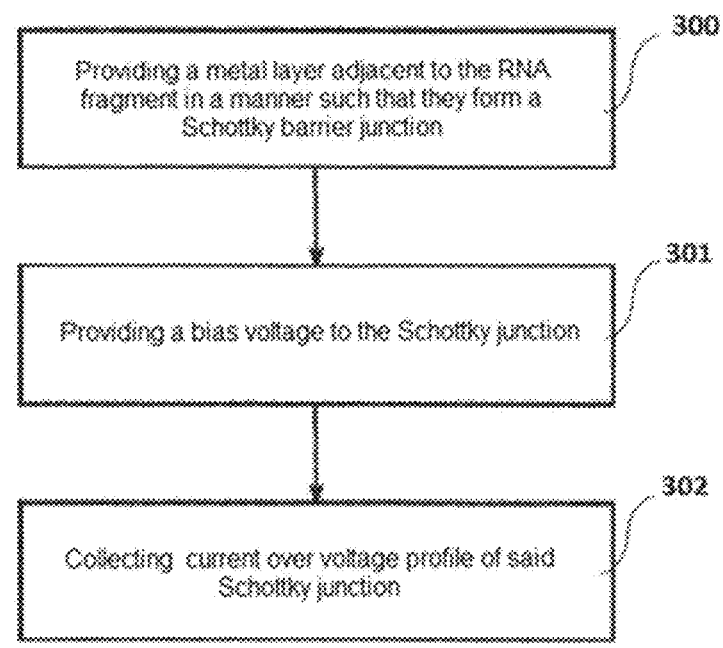
Figure 3:
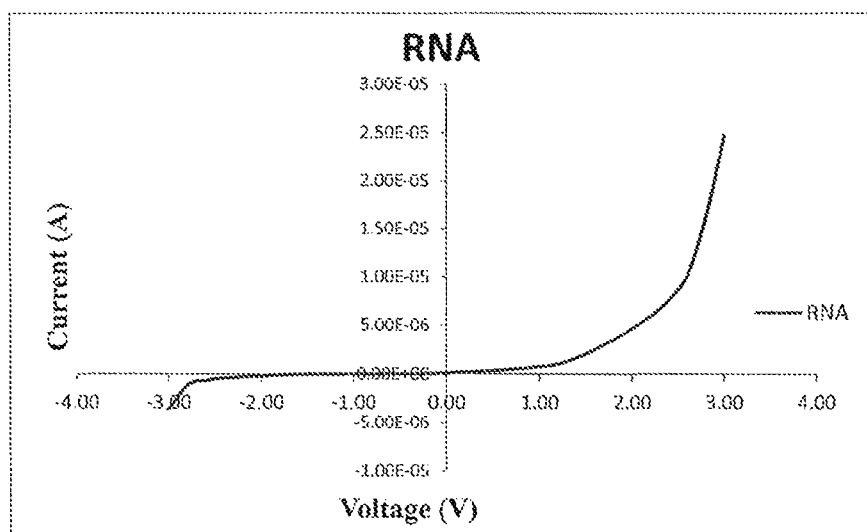

The present invention may be best understood by reference to the following detailed description when read with accompanying drawing in which:

FIG. 1: Overall view of the RNA sample profiling device in accordance with a preferred embodiment of the present invention;

FIG. 2: An example representing the method in accordance with an embodiment of the present invention;

FIG. 3: Depicts an example of the current-voltage characteristics graph of ITO-RNA based Schottky device that can be prepared in accordance with an embodiment of the present invention.

DETAILED DESCRIPTION

The description of a number of specific and alternative embodiments is provided to understand the inventive features of the present invention. It shall be apparent to one skilled in the art, however that this invention may be practiced without such specific details.

It is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting.

Unless defined otherwise, all technical and scientific terms used herein have the same meaning as commonly understood by one of ordinary skill in the art to which this invention belongs.

In a first aspect, and as shown in FIG. 1, the present invention relates to a device for profiling a biological sample with at least one RNA segment comprising: a first metal wire (200) positioned relative to the biological sample (220) such that the sample and the metal wire form a Schottky barrier, unction; a bias voltage provider (not shown) adapted for rectifying the Schottky junction; and; a module for collecting the current over voltage profile of the Schottky junction. In the preferred embodiment, the device further includes a substrate (230) for supporting the sample and a second one metal wire (204) for feeding of bias voltage.

The bias voltage provider is adapted for providing a forward bias voltage; or a reverse bias voltage; whereby the voltage is provided within the range of 0 to 3V as the most suitable detection range. It is anticipated however that other detection or sensing regions may also be present within other bias range. Negative bias voltage may include up to any breakdown voltage in the negative region. Bias voltage devices can be of any conventional devices designed or adapted to feed the predetermined level of bias to the Schottky junction formed by the RNA containing biological sample and the metal wire. In the preferred embodiment, the bias voltage provided is sufficient to rectify the biological sample.

Understandably, when forward bias is required, the positive terminal of the power source i.e. a battery is connected to a p-type material, while the negative terminal is connected to the n-type material. As for reverse bias, positive terminal of the power source is connected to n-type material and the negative terminal is connected to p-type material, such a connection is called reverse bias. A metal wire facilitates the feeding of bias voltage provider. In the preferred embodiment the metal wire may include any one of the following compounds: Aluminium (Al), Aurum (Au), and Cuprum (Cu) and other metals.

The device may include a glass substrate to support the layer of metal (such as Au, Cu, Al etc) or other semiconducting reference material (such as ITO) and biological sample. It is anticipated that the substrate can be of any solid substrate suitable to support the biological sample without affecting the properties of the biological sample. In one embodiment, the ITO layer or any suitable conductive layer is fabricated onto a surface of the substrate by conventional evaporation techniques. This layer can be selected from the following group of materials: Indium Tin Oxide (ITO), Tin Oxide ($SnO_2$) or others.

According to another aspect of the present invention, there is provided a method for profiling a biological sample comprising at least one RNA fragment isolated from a subject comprising: providing a metal wire adjacent to the RNA fragment, in a manner such that they form a Schottky barrier junction; providing a bias voltage to the Schottky junction; and collecting current over voltage profile of said Schottky junction.

In one embodiment, the profiling is preferably conducted in a controlled environment, with a humidity of about 65 to 75 (RH) and room temperature of 25° C. to 27° C. The device is able to capture the semiconductive behaviour of the RNA, hence providing, I-V characteristics based on the profiled RNA fragment from the biological sample. Ideally, the device is adapted for generating quantitative response based on varying bias voltage, subject to the RNA fragment being profiled. The parameters for investigation may vary, for example, but not limiting to, turn-on voltage, shunt resistance, series resistance, barrier height, ideality factor, breakdown voltage, breakdown current etc.

It would be understood that the RNA specimen or sample may be prepared based on standard procedures, whereby fragments or variants of the RNA could be generated using recombinant and/or PCR technology that binds the RNA to the biological sample. Understandably, the biological sample may be obtained from a human, animal or plant subject.

In a further aspect, the present invention provides a method for profiling a biological sample comprising at least one RNA fragment isolated from a subject comprising: providing a metal wire adjacent to the RNA fragment, in a manner such that they form a Schottky barrier junction (300); providing a bias voltage to the Schottky junction (301); and collecting current over voltage profile of said Schottky junction (302). It is anticipated that the device is able to generate varying quantitative responses based on varying bias voltage, subject to the sample being analysed or profiled. An example representing the method in accordance with an embodiment of the present invention is shown in FIG. 2.

The device and method of the present invention may be deployed to identify or detect or profile unknown RNA, whereby the Schottky junction can be of p-n or n-p junction, depending on the type of RNA fragment being profiled.

The following provides experimental examples in relation to the preparation of the profiling method in accordance with an embodiment of the present invention. It should be noted that the experimental examples should not be construed as limitations to the scope of protection.

Example 1

Profiling of RNA Specimen

The RNA, specimen is prepared by taking a fragment or a portion of an RNA test subject, whereby the amount of 10 µL of total RNA, standard procedures were employed to yield pure RNA solution samples. The RNA specimen is then placed adjacent to a part of metal film. Separate metal wires are placed to connect and conduct RNA specimen and metal film, respectively, Bias voltage is provided through these metal wires. I-V monitor is used to capture Schottky I-V profile of Schottky junction, I-V profile shows current vs voltage profile of RNA specimen. This principle and setup is used to detect and sense RNA specimen.

Example 2

Positive and Negative Regions Schottky Profile of an RNA Sample

FIG. 3 depicts an example of the current-voltage characteristics graph of ITO-RNA based Schottky device in accordance with an embodiment of the present invention. As shown, under the forward bias, the current increases exponentially compared to that of the reverse bias region. As shown in FIG. 3 the threshold voltage is estimated at 3V, whereby when applied the forward bias, the current can be seen as increasing exponentially.

The device and method in accordance with the embodiments of the present invention are useful as tools for determining the RNA profiles; which then entails as the discovery of new therapeutic targets, detection of diseases, diagnostics, forensic research, cancer early detection and research and for the screening of novel molecular therapeutic agents. It is however anticipated that the device and method of the present invention can be deployed for any preliminary researches or analysis in the broad spectrum of scientific field.

The present invention is capable of detecting, sensing and identifying various types of RNA from different biological sources. Accordingly, the present invention enables the development of low cost, rapid and extremely sensitive RNA detection/identifying kit based on RNA electronics with an impact in biotechnology, molecular biology, genetics and pathology.

From the foregoing, it would be appreciated that the present invention may be modified in light of the above teachings. It is therefore understood that, within the scope of the appended claims, the invention may be practiced otherwise than as specifically described.

The invention claimed is:

1. A device configured to generate an electrical signal profile of a ribonucleic acid (RNA) segment in a biological sample, the device comprising:
    a metal wire positioned adjacent to the RNA containing biological sample such that the RNA containing biological sample and the metal wire form a Schottky barrier junction;
    a bias voltage provider to rectify the Schottky barrier junction formed by the RNA containing biological sample and the metal wire; and
    a module configured to collect a current over voltage profile of the Schottky barrier junction formed by the RNA containing biological sample and the metal wire, wherein the device is an RNA detection/identifying kit, and depending on a type of RNA segment being profiled, the Schottky barrier junction formed by the RNA containing biological sample and the metal wire is a p-n junction or a n-p junction.

2. The device as claimed in claim 1, wherein the device further comprises a second metal wire to facilitate feeding of bias voltage.

3. The device as claimed in claim 1, wherein the bias voltage provider is configured to provide a forward bias voltage.

4. The device as claimed in claim 1, wherein the bias voltage, provider is configured to provide a reverse bias voltage.

5. The device as claimed in claim 1, wherein the biological sample is supported by a solid substrate.

6. The device as claimed in claim 5, wherein the substrate is glass.

7. The device as claimed in claim 5, wherein the substrate includes a conductive layer formed on the surface of the substrate using evaporation techniques.

8. The device as claimed in claim 1, wherein the bias voltage is provided within the range of 0 to 3V as the detection range.

9. The device as claimed in claim 1, wherein the bias voltage provider includes a metal wire.

10. The device as claimed in claim 1, wherein the device is configured to generate varying quantitative responses based on a varying bias voltage subject to a RNA fragment sequence.

11. The device as claimed in claim 1, further comprising:
    a conductive layer fabricated onto a surface of a substrate, wherein
        the conductive layer is selected from a first material group comprising:
        Indium Tin Oxide (ITO), or Tin Oxide ($SnO_2$), and
        the metal wire is selected from a second material group comprising: Aurum (Au), Cuprum (Cu), or Aluminum (Al).

12. The device a claimed in claim 1, wherein the metal wire is selected from the following group of materials: aluminum (Al), Aurum (Au), or Cuprum (Cu).

13. The device as claimed in claim 1, wherein the device is further configured to identify at least one type of RNA from various types of RNA.

14. A method comprising:
    generating, by an electronic device, an electrical signal profile of a ribonucleic acid (RNA) segment in a biological sample,
    wherein the method of generating, by the electronic device, the electrical signal profile of the RNA segment includes the following method steps;
        providing a metal wire adjacent to the RNA segment, in a manner such that the metal wire and the RNA segment form a Schottky barrier junction;
        providing a bias voltage to the Schottky barrier junction; and
        collecting a current over voltage profile of the Schottky barrier junction, wherein the device is an RNA detection/identifying kit, and depending on a type of RNA segment being profiled, the Schottky barrier junction is a p-n junction or a n-p junction.

15. The method as claimed in claim 14, wherein the provided bias voltage is sufficient to rectify the biological sample.

16. The method as claimed in claim 14, wherein the provided bias voltage is a forward or a reverse bias.

17. The method as claimed in claim 14, furthering comprising:
    identifying, by the device, at least one type of RNA from various types of RNA.

\* \* \* \* \*